United States Patent [19]
Josephson et al.

[11] Patent Number: 5,164,297
[45] Date of Patent: Nov. 17, 1992

[54] SOLVENT MEDIATED RELAXATION ASSAY SYSTEM

[75] Inventors: Lee Josephson, Arlington; Edward T. Menz, Quincy; Ernest V. Groman, Brookline, all of Mass.

[73] Assignee: Advanced Magnetics Inc., Cambridge, Mass.

[21] Appl. No.: 518,567

[22] Filed: May 3, 1990

[51] Int. Cl.$^5$ .............................................. G01N 33/53
[52] U.S. Cl. .................................... 435/7.25; 435/7.1; 436/150; 436/173; 436/517; 436/519; 436/526; 436/806
[58] Field of Search ............... 436/526, 150, 173, 517, 436/519, 806; 435/7.1, 7.25

[56] References Cited

U.S. PATENT DOCUMENTS

| | | | |
|---|---|---|---|
| 3,453,288 | 7/1969 | McConnell | 260/326.8 |
| 3,933,997 | 1/1976 | Hersh et al. | 424/1 |
| 3,959,287 | 5/1976 | Goldstein et al. | 260/285 |
| 4,141,687 | 2/1979 | Forrest et al. | 23/230 R |
| 4,219,335 | 8/1980 | Ebersole | 23/230 B |
| 4,386,054 | 5/1983 | Takenehi | 422/63 |
| 4,452,773 | 6/1984 | Molday | 424/1.1 |
| 4,554,088 | 10/1985 | Whitehead et al. | 252/62.54 |
| 4,661,408 | 4/1987 | Lau et al. | 428/405 |
| 4,795,698 | 1/1989 | Owen et al. | 435/4 |

OTHER PUBLICATIONS

Krick; "Ligand Binder Assays, Labels and Analytic Strategies", Dekker, N.Y., 1985, pp. 233-239.
Willard et al.: "Instrumental Methods of Analysis", Van Nostrand, Princeton, 1965, pp. 160-195.
Thulborn et al.: Biochem. Biophys Acta 714 pp. 265-270.
G. L. Wolf et al. (1985) in *Magnetic Resonance Annual 1985*, H. Y. Kressel, ed. Raven Press, N.Y., pp. 231-266.
Meares et al. (1984) Anal. Biochem. 142 pp. 68-78.
Meares and Wensel (1984) Acc. Chem. Res. 17 pp. 202-209.
Khaw et al. (1980) Science 209 pp. 295-297.
Ogan et al. (1987) Invest. Radiol. 22 pp. 665-671.

*Primary Examiner*—Christine M. Nucker
*Assistant Examiner*—Jeffrey Stucker
*Attorney, Agent, or Firm*—Bromberg & Sunstein

[57] ABSTRACT

A new ligand binding assay is based upon measurements of relaxation rates of the solvent, which are obtained with a magnetic resonance (MR) spectrometer. It is termed a solvent mediated relaxation assay system (SMRAS). SMRAS is based on the observation that the enhancement of proton relaxation rates produced by a magnetic material can be modulated by the binding of various analytes to a magnetic material. Hence the relaxation rate of the solvent can be interpreted to give information on the concentration of an analyte.

17 Claims, 5 Drawing Sheets

SOLVENT MEDIATED RELAXATION ASSAY SYSTEM

TECHNICAL FIELD

The present invention relates to assays using magnetic materials in the presence of a magnetic field and electromagnetic radiation.

BACKGROUND ART

Magnetic materials have been utilized in binding assays in a number of ways.

A. Magnetic Particles as vehicle to separate Free and Bound Labels

One of first applications of magnetic materials to immunoassays involved the attachment of antibodies to magnetic particles. (U.S. Pat. No. 4,554,088, for an invention of Whitehead; U.S. Pat. No. 4,141,687, for an invention of Forrest; U.S. Pat. No. 4,661,408, for an invention of Lau; and U.S. Pat. No. 3,933,997, for an invention of Hersh). This permits separation of the magnetic antibody from bulk solution, by the application of an external magnetic field. After this separation has been accomplished, the amount of material attached to the magnetic antibody is determined. Quantification of the amount bound is accomplished by the use of a label or tracer attached to an antigen. Tracers of varying types have been used, including radioisotopes, enzymes, chemiluminescent labels, fluorescent groups, etc. In this type of application magnetic particles serve as a vehicle for separation. Assays requiring the separation of bound and free labels, followed by quantification of the amount of label bound, are termed heterogenous immunoassays or heterogenous ligand binding assays. In this type of application the magnetic property conferred on the antibody by attachment to a magnetic particle serves to facilitate separation. The same reagents could be used in an assay without a magnet; for example centrifugal force can replace magnetic force as a means of separating magnetic particles from solution.

The magnetic particles for previously described heterogeneous immunoassays are of about a micron in size or larger. The requirement for magnetic materials of at least this size results from the fact that the force on a magnetic particle exerted by an applied magnetic field and magnetic field gradient is proportional to the mass of the magnetic material per particle. Therefore very small particles experience very weak forces from an applied magnetic field. Very small materials move too slowly to be used in assays requiring separation.

B. Magnetic Particles as Labels In Heterogeneous Immunoassay Systems.

A second use of magnetic materials in immunoassays involves its use as a label in a heterogeneous type of ligand binding assay (U.S. Pat. No. 4,219,335, for an invention of Ebersole). In example 1 of this patent an antibody to human IgG is immobilized to a nylon film. The immobilized antibody is exposed to analyte (human IgG), which binds the immobilized antibody. After separation and washing of the film to remove unreacted analyte, anti-IgG tagged with magnetic particles is added. After the magnetic anti-IgG has been allowed to bind to the immobilized analyte (IgG), separation and washing removes unreacted, unbound magnetic particles. The result is a tertiary complex (that forms if analyte is present and the magnetic particle on the nylon film is detected in a suitable instrument). This tertiary complex may be described as follows:

Immobilized antibody-human IgG-magnetic antiIgG where the symbol (-) denotes a noncovalent, potentially reversible association between two entities.

In its use of separation of free and bound analyte, the protocol of Ebersole is an example of a heterogeneous immunoassay. A magnetic antibody is used as a label and is detected on the solid phase after separation of bound and free ligand. The magnetic particle acts as a label, replacing radioactive, enzymatic, chemiluminescent or fluorescent labels.

C. Electron spin Resonance (EsR) Immunoassay

ESR immunoassay involves the covalent attachment of materials which include an unpaired electron to drugs or hormones. The resulting compound is referred to as a spin-labeled drug or spin-labeled hormone. Most often these are free radicals, and most commonly a cyclical nitroxide group. Often the analyte detected in ESR immunoassay is a drug. When an antibody to a drug binds the spin-labeled drug derivative, the movement of the spin label in solution is altered, and this altered motion results in changes in the ESR spectrum. Competition of the drug (analyte) prevents binding of the spin-labeled drug derivative, in the usual manner of competitive immunoassays. Since no separation is required, ESR immunoassay is a homogeneous type of assay. Electron spin immunoassay has recently been reviewed, see Krick, L. J. "Ligand Binder Assays, Labels and Analytic Strategies" Marcel Dekker, New York, 1985 pp. 233-239.

PRINCIPLES AND SUMMARY OF THE INVENTION

The present invention provides a ligand binding assay based upon measurements of relaxation rates of the solvent, which are obtained with a magnetic resonance (MR) spectrometer. It is termed a solvent mediated relaxation assay system (SMRAS). SMRAS is based on the observation that the enhancement of proton relaxation rates produced by a magnetic material can be modulated by the binding of various analytes to a magnetic material. Hence the relaxation rate of the solvent (i.e., of the protons in water, for example) can be interpreted to give information on the concentration of an analyte.

It has been often observed that the addition of magnetic materials having a positive magnetic susceptibility to a solvent increases the relaxation rate(s) of nuclei measured with a magnetic resonance (MR) spectrometer. [See G. L. Wolf et al. in *Magnetic Resonance Annual* 1985, H. Y. Kressel, ed. Raven Press, N.Y., 1985, pp. 231-266.] The ability to increase relaxation rates is the physical property of magnetic materials which makes them useful as contrast agents in MR imaging. Instruments such as the MR spectrometer measure the relaxation rates of nuclei in a sample and are used to assess the ability of magnetic materials to alter relaxation rates. Water is the most general solvent and the effect of a magnetic material on the relaxation of water protons is most often measured. The relaxation of protons is of two types, the so-called spin-lattice relaxation rate denoted $1/T1$, or the spin-spin relaxation, denoted $1/T2$. In SMRAS the binding of an analyte to a magnetic material alters the effect the magnetic material exerts on solvent relaxation rates, which are measured and interpreted to determine the concentration of analyte.

Many different kinds of biological and nonbiological molecules can be utilized in SMRAS. SMRAS often utilizes a molecule of biological origin and modifies the molecule through the attachment of a magnetic moiety, capable of altering solvent relaxation. Examples of biological molecules that can be utilized in this manner include carbohydrates, lectins, antibodies, receptors, antigens, proteins, binding proteins, nucleic acids, drugs, pesticides, etc. The magnetic moiety utilized in SMRAS can be any material capable of altering solvent relaxation as discussed below. Examples of nonbiological molecules that can be utilized in SMRAS include metal ion chelators.

In many cases, the changes in solvent relaxation rates that are measured in SMRAS reflects the formation of (or the dissolution of) large, extended complexes consisting of many magnetic particles and many analyte molecules. (The term "particle" is used to mean any material above about 5 nm in diameter.) Such complexes form in example 3, where addition of the analyte dextran breaks up the complex between Con A, a multivalent lectin binding dextran, and a dextran-coated superparamagnetic iron oxide. Similarly in example 4, bovine serum albumin (BSA) acts to dissolve or break up a complex between antibody to BSA and a BSA coated superparamagnetic iron oxide.

Some versions of SMRAS are similar to conventional immunoassays that are based on the formation or dissolution of large, extended macromolecular complexes. Complexes between antigens and antibodies are used in nephelometry; the complexes between antibodies and red blood cells are used in hemagglutination assays; complexes between antibody coated latex particles and antigens are used in particle counting immunoassays. SMRAS is different from such conventional assays in that it uses the magnetic resonance properties of the solvent to detect complex formation, and does not use radiation at or near the frequency of visible or ultraviolet light.

In some cases, the binding reactions of SMRAS do not involve the formation of large macromolecular aggregates. In example 1 magnesium (the analyte) replaces manganese in complexation with a chelator, without formation of a macromolecular complex. In all cases SMRAS uses the change in solvent relaxation rates exerted by a magnetic material to determine the concentration of an analyte.

In SMRAS, an MR spectrometer is used to measure the relaxation rates of water protons. For a review of MR and ESR spectrometers see Willard, H. H. et al. "Instrumental Methods of Analysis" Van Nostrand, Princeton, 1965, pp. 160-195. An MR spectrometer places the sample in a uniform applied magnetic field, and subjects it to pulses of radiofrequency radiation, applied at a specific frequency, referred to as the Larmor frequency of the water protons. The signal obtained from the water protons resulting from absorption of the pulse of radiation is recorded, and the loss of signal (decay) is analyzed to obtain the spin-lattice relaxation rate, and/or the spin-spin relaxation rate.

The distinguishing feature of SMRAS is that analyte concentration is determined from the effects a magnetic material exerts on the relaxation rates of solvent molecules. Hence we term our invention a solvent mediated relaxation assay system. In SMRAS the electromagnetic radiation interacts with the solvent, rather than with a complex of any sort between the analyte and a molecule that binds the analyte. Thus, in many conventional ligand binding assays, the incident radiation interacts directly with a complex formed between the analyte and an antibody or binding protein. Conventional ligand binding assays of this type include nephelometry, hemagglutination, latex agglutination assays and others.

The frequency of the electromagnetic radiation used in SMRAS, however, is matched to the Larmor precession frequency of the solvent, which in turn is determined by the magnetic field of the MR spectrometer. Because the radiation is at the Larmor precession frequency of the solvent, and not matched to the properties of the magnetic label employed, SMRAS can utilize many different types of magnetic materials. Though water is the most common solvent and can be used in SMRAS, other solvents might be employed containing either protons or other MR active nuclei. In an alterative embodiment, a small molecule might be added to the water whose relaxation would be enhanced by the magnetic binding element. For example, ions including the nuclei of certain isotopes (e.g. $^{23}Na^+$), phosphorous (e.g. $H_2^{31}PO_4$) and fluorine (e.g. $^{19}F^-$) exhibit nuclear magnetic resonance and have a high isotopic abundance. All are compatible with aqueous solvents. (Of course, other ions may be used, provided that they include the indicated isotopes of these elements or other isotopes of suitable elements exhibiting nuclear magnetic resonance.) The relaxation rates of such nuclei, like the relaxation rates of solvent protons, are enhanced by magnetic materials exhibiting a positive magnetic susceptibility. For each of the above nuclei, the incident radiation used must be at the appropriate Larmor frequency, so it may be absorbed. In the case of this small-molecule mediated relaxation assay, as in the case of the solvent mediated assay the assay is not dependent on the interaction of incident radiation with a complex between the analyte and a magnetic material. For example, in example 4 below, incident radiation does not react with the resultant magnetic BSA-antibody complex. In each case, the assay depends on the change in relative rate of the nuclei in the solvent or in the small-molecule included in the solvent exerted by the magnetic material.

The electromagnetic radiation used in MR applications, and in SMRAS, is of very low frequency (1 to 100 MHz). Radiation at this frequency is extremely safe, as the widespread use of clinical magnetic resonance imaging indicates. It should not be confused with radiation at other frequencies ($10^{11}$ to $10^{12}$ MHz), that pose safety concerns.

A principal difference between SMRAS and ESR assay methods lies in the frequency of the radiation used. The ESR spectrum is obtained when the sample is placed in a magnetic field and subjected to electromagnetic radiation in the microwave range ($10^4$–$10^6$ MHz). The radiation used in SMRAS is of far lower frequency (1–$10^2$ MHz) than employed by ESR spin immunoassay. The frequency of radiation used in ESR relative to MR based SMRAS is related to a fundamental physical fact: the difference between energy states of unpaired electrons is far greater than the difference between energy states for nuclei exhibiting magnetic resonance.

In contrast to ESR immunoassay techniques, SMRAS uses radiation that is absorbed by the protons of the nonmagnetic (actually diamagnetic) solvent. In ESR immunoassay techniques, the radiation used is absorbed by the unpaired electron of the spin-labeled drug, which may or may not be bound to the antibody, depending on the concentration of analyte present.

Unlike prior art using magnetic separation strategies, the magnetic materials of the current invention are not separated from solution by an external magnetic field, during the assay. In fact many of the magnetic materials used in the invention, including paramagnetic ions, paramagnetic chelates, paramagnetic proteins and superparamagnetic colloids (below the micron size range), cannot be separated from solution in a timely fashion with the magnet fields produced by common permanent magnets.

BRIEF DESCRIPTION OF THE DRAWINGS

The foregoing features of the invention may be more readily understood by reference to the following detailed description taken with the accompanying drawings, in which.

DETAILED DESCRIPTION OF SPECIFIC EMBODIMENTS

A Utility of SMRAS

SMRAS has major advantages over other types of ligand binding assays.

First, SMRAS can work on opaque fluids, whole blood, milk, lipemic plasma, hemolyzed blood, etc. With conventional ligand assays, the optical quality of the samples necessitates preparation to remove interfering substances, before the ligand binding assay protocol can commence.

To obtain the relaxation rates of a solvent, SMRAS utilizes an MR spectrometer. This instrument places the sample in a strong magnetic field and subjects it to radiofrequency radiation at the so-called Larmor frequency of the solvent protons. SMRAS utilizes electromagnetic radiation in the radiofrequency range rather than in the visible range, for the detection of the ligand binding. The indifference of SMRAS to properties of the solvent is due to the fact that the radiofrequency radiation used in the measurement of proton relaxation penetrates most biological systems. In MR imaging the penetrability of radiofrequency radiation is used to advantage. For example the protons in bone marrow proteins can be excited with radiofrequency radiation that has passed through bone and an MR image of bone marrow obtained.

Second, SMRAS is a homogeneous type assay. That is, the assay protocol does not involve a separation of bound and free ligands. This lack of a separation step results in a more user friendly, less labor intensive assay procedure.

Third, SMRAS can measure widely different types of materials as analytes, including materials with different molecular weights and different physicochemical properties. In example 1, below, an assay for a low molecular weight divalent cation (magnesium), is demonstrated. In example 2 an assay for a monosaccharide, in this case glucose, is demonstrated. In example 3 an assay for a polysaccharide polymer, in this case dextran, is demonstrated. In example 4 an assay for protein of about 65,000 daltons (BSA) is demonstrated.

Fourth, a wide variety of magnetic materials including superparamagnetic iron oxide colloids, paramagnetic chelates, paramagnetic ions, paramagnetic red blood cells, or ferromagnetic particles, can be used in SMRAS. These vastly different materials all exhibit a positive magnetic susceptibility, and because of their positive magnetic susceptibility increase relaxation rates of solvent protons. By altering their effect on solvent relaxation rates, all can be utilized in SMRAS. The ability of SMRAS to utilize different types of magnetic materials is shown in the examples below. In example 1, paramagnetic manganese ion, which has a molecular weight of less than 100 daltons, is used to alter solvent relaxation. In example 3 a dextran coated superparamagnetic iron oxide colloid, which has a molecular weight in excess of 500,000 daltons, is used. The superparamagnetic iron oxide possesses a far higher magnetic susceptibility than the paramagnetic manganese ion, although both may be employed.

Fifth, SMRAS offers the possibility of performing multiple ligand binding assays simultaneously, by utilizing many of the data reduction and instrumentation techniques developed for MR imaging. For example, in MR imaging the magnitude of the applied magnetic field can be varied, so that only the protons in different samples resonate at slightly different Larmor frequencies. In MR imaging this is referred to as slice selective excitation. In SMRAS the corresponding technique involves simultaneously placing several sample tubes in a spectrometer that applies a slightly different magnetic field to each sample. As a result protons in each sample will resonate at different Larmor frequencies. The relaxation rates of multiple samples can be determined simultaneously.

There are several general strategies for synthesizing magnetic materials for use in the present invention.

1. Coupling paramagnetic ions to drugs, proteins, carbohydrates, nucleic acids, or other biologically active groups:

Paramagnetic ions are often attached to molecules by derivatization of the molecule with a chelator, followed by allowing the chelate to bind a paramagnetic ion. Examples of this approach include Mears et al. Anal. Biochem. 142:68–78 (1984); Mears and Wensel, Acc. Chem. Res. 17:202–209 (1984); Khaw et al. Science 209:295–297; Ogan et al, Invest. Radiol. 22:665–671 (1987).

2. Coupling magnetic particles or magnetic colloids to drugs, proteins, carbohydrates, nucleic acids, or biologically active groups:

There are a variety of techniques for attaching molecules to magnetic particles and/or colloids such as U.S. Pat. No. 4,141,687, for an invention of Forrest; U.S. Pat. No. 4,661,408, for an invention of Lau; U.S. Pat. No. 4,452,773, for an invention of Molday; U.S. Pat. No. 4,795,698, for an invention of Owen; U.S. Pat. No. 4,554,088, for an invention of Whitehead; and U.S. Pat. No. 3,993,997, for an invention of Hersh.

In the present invention examples 2, 3 and 4 utilize magnetic colloids.

3. Using red blood cells as magnetic "particles":

The paramagnetism exhibited by the deoxyhemoglobin of red blood cells permits the cells to act as magnetic particles, i.e. red blood cells filled with deoxyhemoglobin alter solvent relaxation rates obtained with the MR technique (Thulborn et al. Biochim. Biophys. Acta 714:265-270 (1982)). Assays of red blood cell surface antigens are the basis of blood typing performed prior to blood transfusion. Such assays often involve the agglutination of red blood cells by antibodies, with an optical measurement of agglutination. This red blood cell magnetic agglutination is analogous to the aggregation or dispersion of other magnetic labels used in SMRAS. Thus red blood cells can be utilized in a SMRAS assay without chemical modification to confer a positive magnetic susceptibility upon them.

B. Examples

Example 1

Assay for Magnesium Ion

Background and Principle of the Method

Paramagnetic $Mn^{2+}$ is a powerful enhancer of proton relaxation. When manganese is bound to a chelating compound such as diethylenetriaminepentaacetic acid, DTPA, its ability to enhance proton relaxation is greatly reduced. Magnesium ion ($Mg^{2+}$) is a diamagnetic ion that also binds to DTPA, but which has virtually no effect on proton relaxation, whether bound to DTPA or not. When added to appropriate concentrations of DTPA and manganese, magnesium prevents the binding of manganese to DTPA as shown below.

DTPA—Mn+$Mg^{+2}$→DTPA—Mg+$Mn^{+2}$

As a result the concentration of manganese ion is increased and an increase in 1/T2 results.

Assay Procedure

Figure 1:
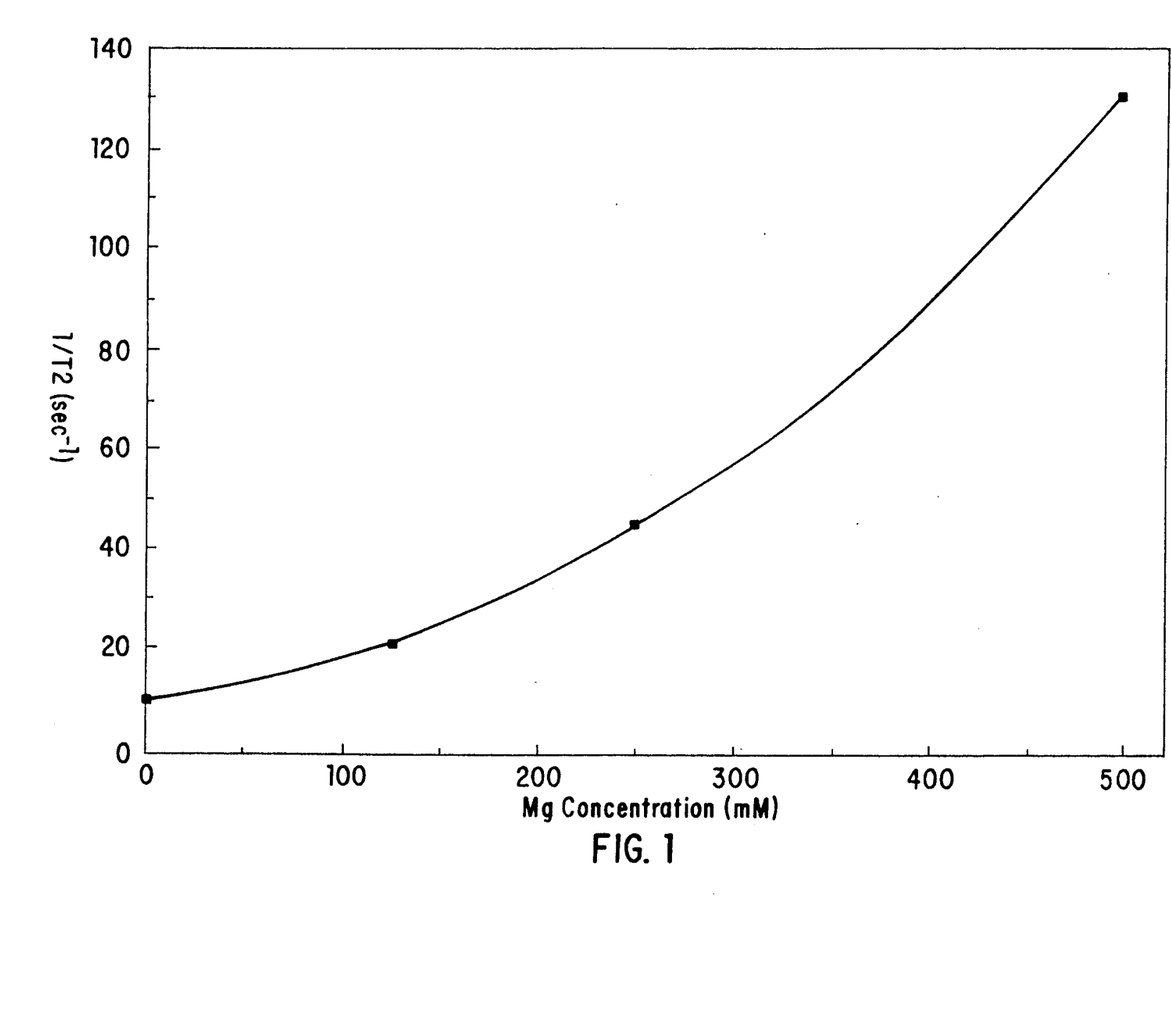
FIG. 1 plots concentration of the analyte (magnesium) in example 1 below versus MR relaxation time of the solvent.

To a test tube was added 0.5 mL of 25 mM DTPA adjusted to pH 8.5 with NaOH, and 0.5 mL of 12.5 mM $MnCl_2$. $MgCl_2$ at various concentrations (0.2 mL) was then added. The solutions were vortexed and the value of 1/T2 determined. The standard curve of FIG. 1 was obtained. All relaxation rate measurements are obtained in an IBM PC-20 MR spectrometer at 39° C., using the Carr Purcell Meiboom Gill (CPMG) technique.

Example 2

Assay for Glucose

Background and Principle of the Method

Conconavalin A (Con A) is a lectin that binds carbohydrates such as dextran. The dextran coated superparamagnetic iron oxide was synthesized by the method of Molday, see above. Monosaccharides like glucose can bind Con A and prevent Con A from binding a dextran coated superparamagnetic iron oxide.

When con A binds a dextran coated superparamagnetic iron oxide, the effect the colloid exerts on 1/T2 increases at low concentrations of Con A but then decreases at higher concentrations (data not shown). In this example concentrations of Con A and superparamagnetic iron oxide have been chosen to maximize the effect the colloid exerts on 1/T2. Under these conditions the addition of glucose breaks up the Con A-dextran coated superparamagnetic iron oxide complex, and reduces 1/T2. This is represented below. (The symbol (/) indicates a permanent bond between two materials under conditions of the assay, while the symbol (—) indicates a dissociable bond.)

Assay Procedure

Figure 2:
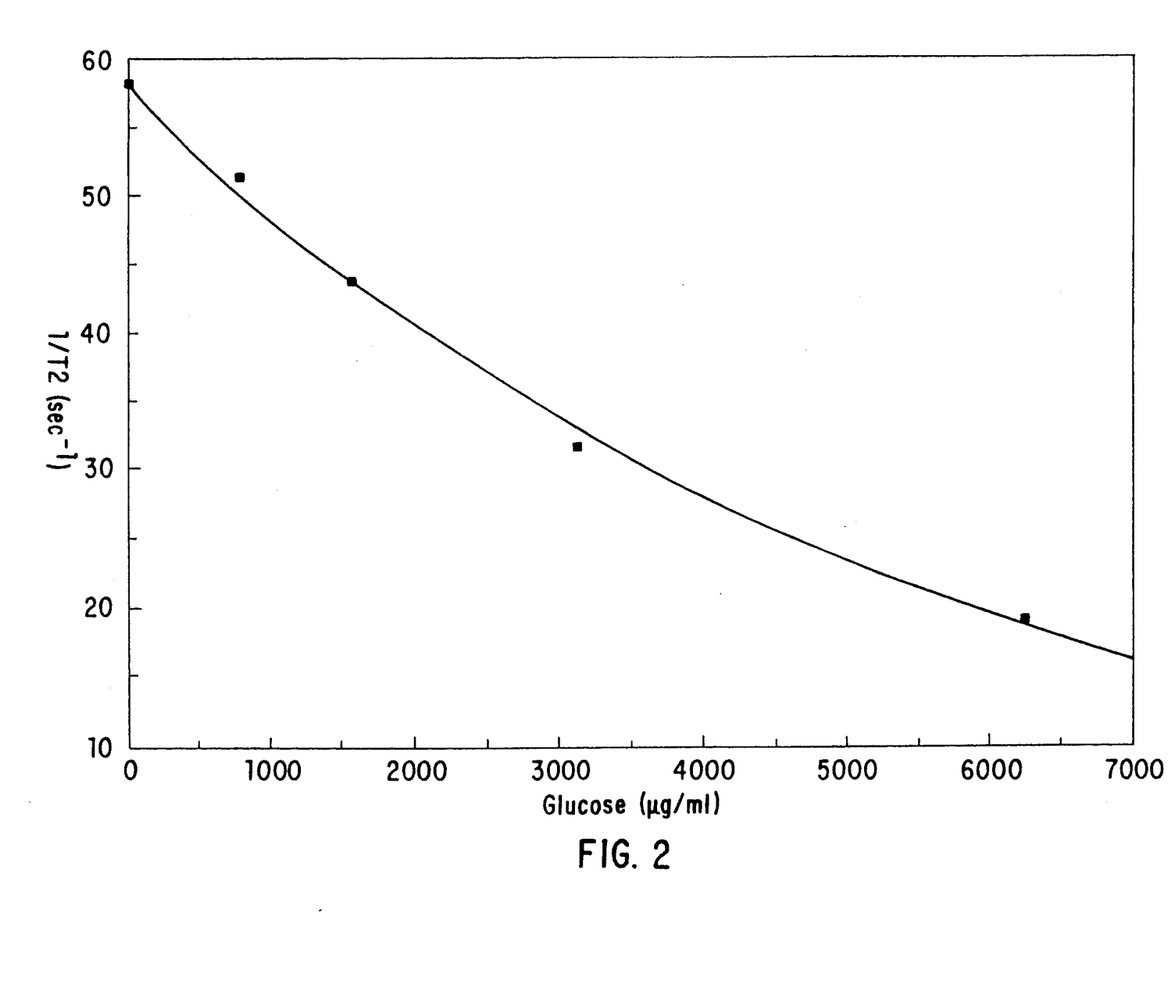
FIG. 2 plots concentration of the analyte (glucose) in example 2 below versus MR relaxation time of the solvent.

Half an mL of Con A (1 mg/mL), 0.5 mL of dextran coated superparamagnetic iron oxide (0.8 mM iron) were mixed together in a test tube and then 0.2 mL glucose, 0 to 200 mg/mL, was added. After 20 minutes at 37° C., relaxation rates were measured as in example 1. The response of the assay to glucose is shown in FIG. 2.

Example 3

Assay for Dextran

Background and Principle of the Method

The procedure is as in Example 2, except that the dextran replaces glucose in favoring the dissociation of the complex between dextran coated superparamagnetic iron oxide and Con A.

Assay Procedure

Figure 3:
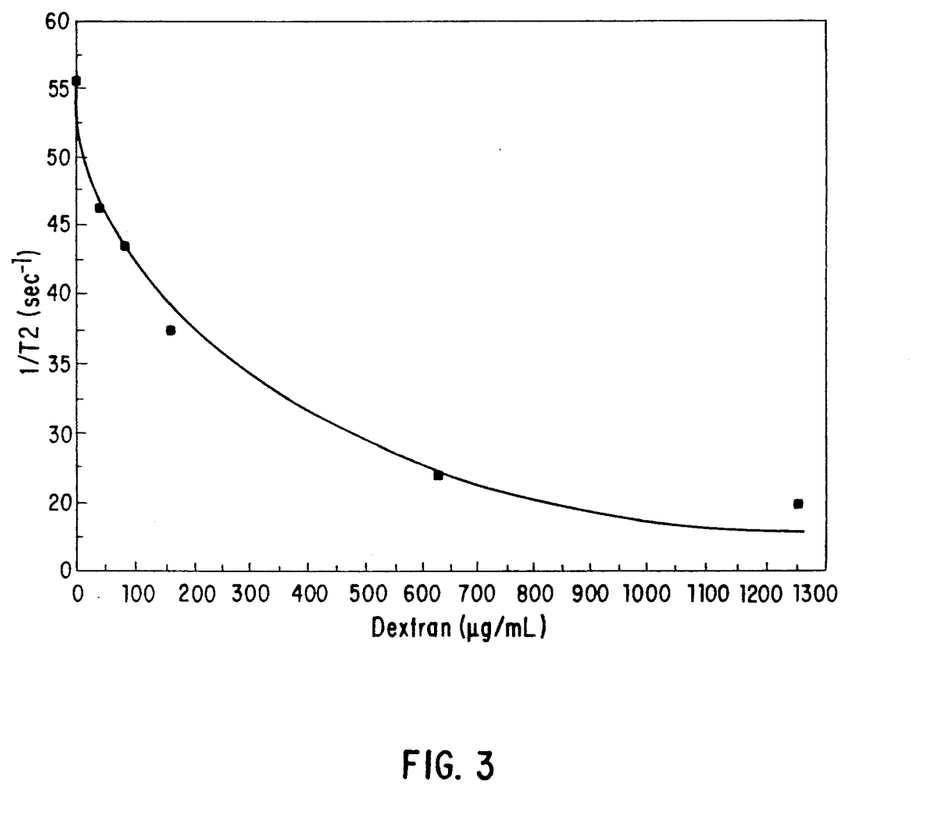
FIG. 3 plots concentration of the analyte (dextran) in example 3 below versus MR relaxation time of the solvent.

The procedure of example 2 is followed except that a dextran T-10, replaces glucose. The response of the assay to dextran is shown in FIG. 3.

Example 4

Assay For Bovine Serum Albumin (BSA) Using Antibody to BSA

Background and Principle of the Method

A BSA coated superparamagnetic iron oxide colloid is utilized and reacted with antibody to BSA. Concentrations of antibody and colloid are chosen such that the presence of antibody decreases the effect the colloid exerts on 1/T2. Addition of BSA favors the dissociation of the antibody from the BSA coated superparamagnetic iron oxide. The addition of BSA increases the value of 1/T2. The reaction might be represented:

Iron Oxide/BSA−Ab+BSA→Iron Oxide/BSA+Ab−BSA

Assay Procedure

A solution of BSA (0.1 mL) at the indicated concentration in phosphate buffered saline with 0.15% gelatin (PBS-gel) is added to a test tube. Next 0.1 mL of BSA coated superparamagnetic iron oxide colloid is added. The colloid used was the BSA-coated particle from Immunicon Corp., (Huntington Valley Pa.). Finally, 0.1 mL of anti-BSA is added. The antibody was diluted 1:40 in PBS-gel and was from Sigma Chemical (St. Louis, Mo.).

Figure 4:
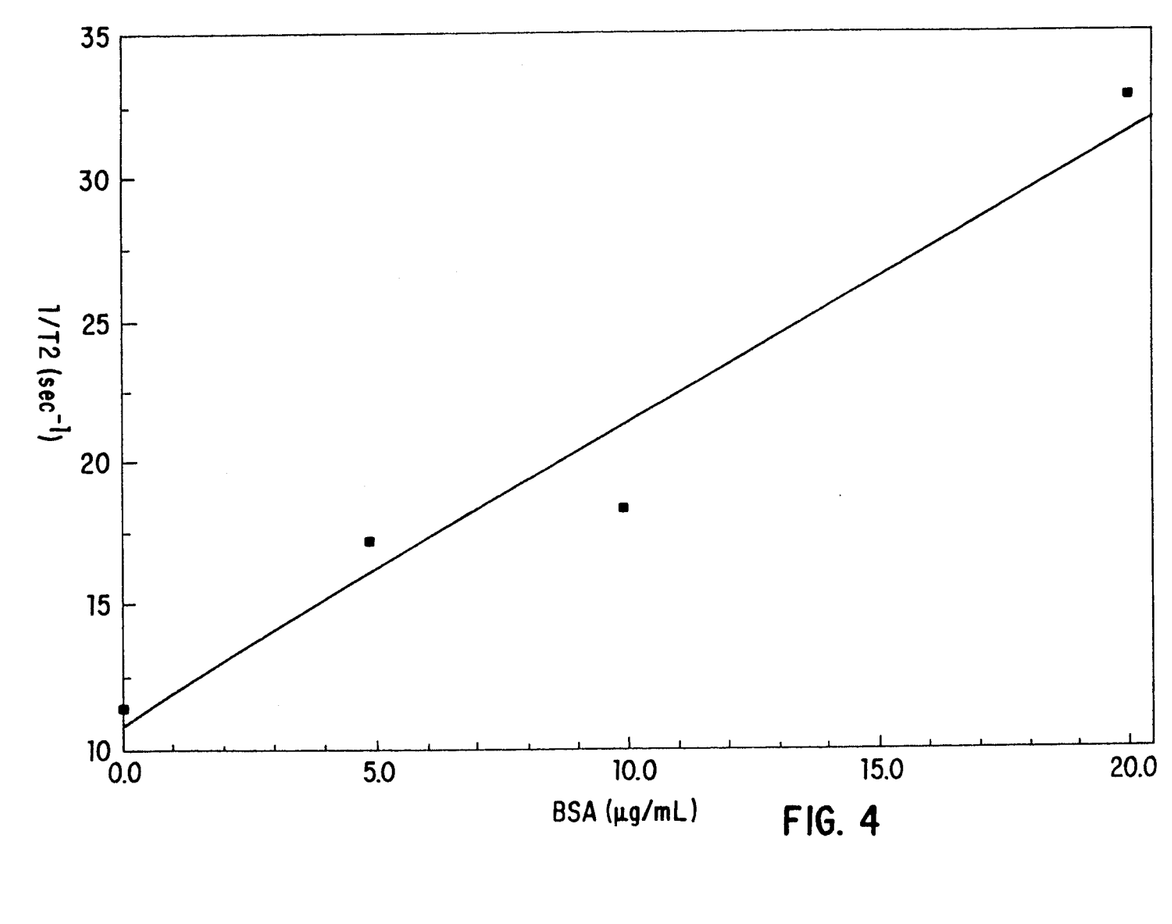
FIG. 4 plots concentration of the analyte (BSA) in example 4 below versus MR relaxation time of the solvent.

The mixture is incubated at 37° C. for 60 minutes and the relaxation rate (1/T2) of the 300 mL sample determined as above. The standard curve for the assay is shown in FIG. 4.

Example 5

Assay for Chelating Equivalent Groups on a Protein

Background and Principle of the Method

In this example DTPA anhydride is reacted with the protein fetuin from calf serum, to given a high molecular weight protein chelator denoted Fet/DTPA. The assay involves ascertaining the capacity of the modified protein (Fet/DTPA) to decrease 1/T2 by comparing its effect with solutions of DTPA in known concentrations. This is represented below.

$$Fet/DTPA + Mn^{+2} \rightarrow Fet/DTPA-Mn$$

or $$DTPA + Mn^{+2} \rightarrow Mn-DTPA$$

Assay Procedure

1. Synthesis of Fet-DTPA

Fifty mg of fetuin is dissolved in 10 mL of 0.1M NaHCO$_3$, pH 8 buffer and 120 mg of DTPA anhydride added. Unreacted DTPA was removed by dialysis against the same buffer using a dialysis bag with a 10 kilodalton cutoff.

2. Assay Procedure

Figure 5:
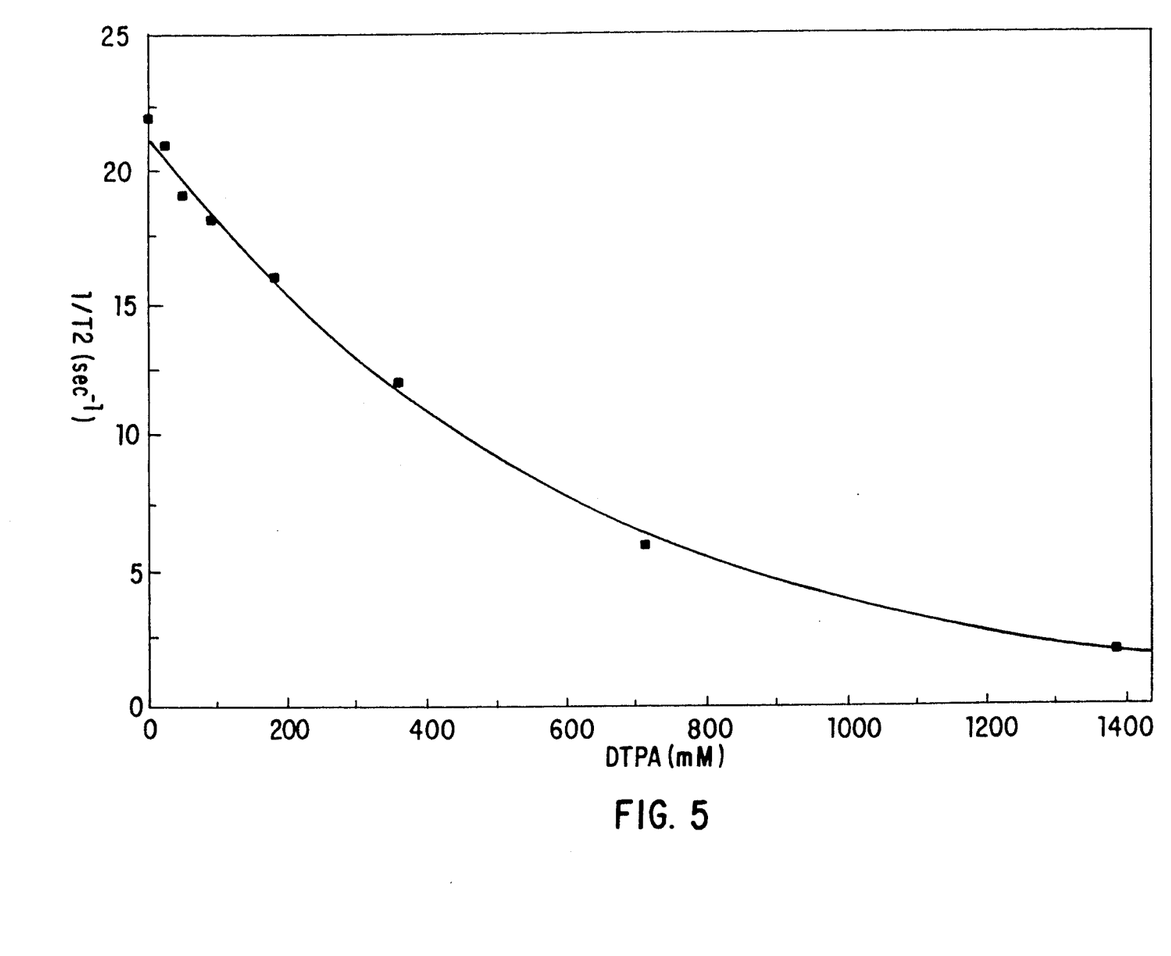
FIG. 5 plots concentration of the analyte (DTPA) in example 5 below versus MR relaxation time of the solvent.

To a test tube is added 0.2 mL of 1 mM MnCl$_2$, 0.2 mL DTPA solutions at known concentrations (0-5600 nM) or 0.2 mL of Fet-DTPA (2mg/mL in fetuin but with unknown amount of DTPA). The reaction mixture is incubated at room temperature for 30 minutes after which values of 1/T2 are determined. The standard curve shown in FIG. 5 was obtained for DTPA. The number of equivalent chelating groups on the protein was determined from the effect of a comparable concentration of DTPA.

What is claimed is:

1. A method, of assaying the concentration of an analyte in a solvent "in vitro", comprising:
    providing a magnetic material having positive magnetic susceptibility to alter the relaxation characteristics of the solvent nuclei of a component included in the solvent, such relaxation characteristics obtained by a magnetic resonance technique, the magnetic material being selected so that its effect, on the relaxation of the nuclei of the component included in the solvent, is modified by the interaction of the analyte with the magnetic material;
    causing the magnetic material and the analyte to be located in the solvent;
    allowing the magnetic material to interact with the analyte; and
    measuring the relaxation characteristics of the nuclei of the component by a magnetic resonance technique.

2. A method according to claim 1, wherein the magnetic material is a magnetic metal oxide colloid or magnetic particle, with a polymer coated-surface.

3. A method according to claim 1, wherein the magnetic material is a protein with a paramagnetic ion attached.

4. A method according to claim 1, wherein the magnetic material is a red blood cell.

5. A method according to claim 1, wherein the magnetic material is a paramagnetic ion.

6. A method according to claim 1, wherein the magnetic material is a magnetic antibody.

7. A method according to claim 1, wherein the magnetic material is a magnetic antigen.

8. A method according to claim 1, wherein the component included in the solvent is the solvent itself.

9. A method according to claim 2, wherein the component included in the solvent is the solvent itself.

10. A method according to claim 3, wherein the component included in the solvent is the solvent itself.

11. A method according to claim 4, wherein the component included in the solvent is the solvent itself.

12. A method according to claim 5, wherein the component included in the solvent is the solvent itself.

13. A method according to claim 6, wherein the component included in the solvent is the solvent itself.

14. A method according to claim 7, wherein the component included in the solvent is the solvent itself.

15. A method according to claim 1, wherein the component included in the solvent is an ion that includes the isotope of sodium having an atomic weight of 23.

16. A method according to claim 1, wherein the component included in the solvent is an ion that includes the isotope of phosphorous having an atomic weight of 31.

17. A method according to claim 1, wherein the component included in the solvent is an ion that includes the isotope of fluorine having an atomic weight of 19.

* * * * *